United States Patent [19]

Rauh

[11] Patent Number: 5,693,020
[45] Date of Patent: Dec. 2, 1997

[54] HOSE PUMP FOR THE EXACT DOSING OF SMALL QUANTITIES OF LIQUIDS

[75] Inventor: Erwin Rauh, Poing, Germany

[73] Assignee: Loctite Europa E.E.I.G. (E.W.I.V.), Hochbrück, Germany

[21] Appl. No.: 508,597

[22] Filed: Jul. 28, 1995

[30] Foreign Application Priority Data

Jul. 28, 1994 [DE] Germany ............... 9412228 U

[51] Int. Cl.⁶ .................................................. A61M 1/00
[52] U.S. Cl. .......................................... 604/151; 604/131
[58] Field of Search ......................... 604/131, 151, 604/152, 153, 154; 417/474

[56] References Cited

U.S. PATENT DOCUMENTS

| 3,990,444 | 11/1976 | Vial | 128/214 F |
| 4,025,241 | 5/1977 | Clemens | 417/474 |
| 4,214,681 | 7/1980 | Levine | 222/214 |
| 4,660,607 | 4/1987 | Griffith et al. | 141/1 |

FOREIGN PATENT DOCUMENTS

| 367874 | 12/1981 | Austria . | |
| 120284 | 10/1984 | European Pat. Off. | 604/131 |
| 319277 | 7/1989 | European Pat. Off. | 604/151 |
| 23 58 228 B2 | 5/1974 | Germany . | |
| 25 41 892 A1 | 4/1976 | Germany . | |
| 29 44 186 C2 | 5/1981 | Germany . | |
| 33 44 848 A1 | 6/1985 | Germany . | |
| 37 26 452 A1 | 2/1989 | Germany . | |
| 1110929 | 8/1984 | U.S.S.R. | 417/474 |
| 1716192 | 2/1992 | U.S.S.R. | 417/474 |
| 2 076 068 | 11/1981 | United Kingdom . | |

OTHER PUBLICATIONS

J. H. Williams, "Peristaltic Roller Pump," IBM® Technical Disclosure Bulletin, vol. 20, No. 3, Aug. 1977.

*Primary Examiner*—Sam Rimell
*Assistant Examiner*—Luke Yeh
*Attorney, Agent, or Firm*—Steven C. Bauman; Eugene F. Miller

[57] ABSTRACT

A hose pump has a hose bed (24) and a number of rollers (25) wich are housed in rotatable manner on a rotary-driven roller holder (22) on a pitch circle (21) and are moved by the roller holder (22) on an orbital path at a distance from the hose bed (24). That distance is chosen such that the rollers (22) can compress a hose (14), which lies between the hose bed (24) and the orbital path of the rollers (22), on one part of their orbital path. The hose bed (24) is arranged offset vis-á-vis the orbital path of the rollers (22) so that the distance between the hose bed (24) and the orbital path of the rollers (22) increases in the direction of movement of the rollers (22).

17 Claims, 2 Drawing Sheets

HOSE PUMP FOR THE EXACT DOSING OF SMALL QUANTITIES OF LIQUIDS

The invention relates to a hose pump for the exact dosing of small quantities of liquids. The hose pump contains a hose bed and a number of rollers which are housed on a rotary-driven roller holder rotatable on a pitch circle of the roller holder and are moved by the roller holder on an orbital path at a distance from the hose bed, whereby the distance is chosen such that the rollers can compress a hose which is arranged between the hose bed and the orbital path of the rollers at one part of their orbital path.

Such hose pumps are generally known. They are used in particular in the medical sector, e.g. for dialysis and with heart-lung machines since the liquid to be pumped, in this case the blood, only comes into contact with the hose wall and not with other surfaces. Hose pumps have a very simple mechanical structure. With the known hose pumps, accurate measurement of the size of individually dispensed drops is not possible. This is to be attributed to the fact that the liquid is pumped intermittently, in accordance with the frequency of the pressure pulses exerted by the rollers onto the hose.

The object of the invention is to improve the dosability of the delivery capacity of a hose pump and to achieve a uniform delivery of the liquid.

According to the invention, this object is achieved by arranging the hose bed in offset manner vis-à-vis the orbital path of the rollers, so that the distance between trough and roller orbital path increases in the direction of movement of the rollers.

The hose bed is preferably offset by approximately the internal diameter of the hose vis-à-vis the roller orbital path.

Because the distance between the trough of the hose bed and the roller orbital path increases in the direction of delivery, the point of maximum contact pressure is eccentric, i.e. it is displaced from the centre of the trough towards the direction of delivery. In general, the point of maximum contact pressure on the hose is at the start of the trough and the hose opens conically because of the expanding distance between trough and roller orbital path. As a result, the pump surges are dampened and an almost continuous pump behaviour is achieved.

The hose pump according to the invention is suitable in particular for the dispensing of very small quantities of liquids, e.g. for the reproducible dispensing of individual drops of an adhesive. For the dispensing of each drop, the roller holder is further rotated by a certain step angle. The quantity produced, i.e. the drop size, depends in the first instance on the step angle which the roller holder describes for this produced quantity. The division of the roller holder and the step angle are expediently selected such that the step angle is not the same as the division of the roller holder (360°/number of rollers), nor a fraction or a multiple thereof.

In establishing the number of rollers, it must also be ensured that the mechanical system of the hose pump and the electrical system of the drive motor are uncoupled as far as possible to avoid unfavourable oscillation behaviour. The following equation results for the step angle:

$$\text{Step angle} \neq 2k \cdot 360°/n \quad n = \text{number of rollers} \quad k=1/m \ldots 1 \ldots i$$
$$m \in \infty \ldots 2; \ i \in 2 \ldots \infty$$

It follows from this equation that an odd number of rollers is more expedient since far fewer system conditions are to be excluded with this than with an even number of rollers in order to avoid cyclic operations in the volume flow.

When fixing the number of rollers and the division of the roller holder it is to be ensured that there are always at least three rollers within the hose bed. The continuity of delivery is thereby also improved.

The yield quantity is essentially also determined by the internal diameter of the hose. By appropriate selection, the hose pump according to the invention can be set in particular to dispense particularly small quantities of liquids, down into the µ-litre range. The hose pump according to the invention is thereby suitable for the repeatedly accurate dispensing of very small quantities of liquids, e.g. skin adhesive, as is used in skin surgery.

A bubble detector which generates a signal if air or gas bubbles or small solid foreign bodies are conveyed in the hose is preferably connected upstream of the hose pump. The bubble detector contains a light source, which directs a beam of light transversely through the hose, the diameter of the light beam corresponding to the internal diameter of the hose. On the other side of the hose the light beam strikes a receiver. Infra-red light is preferably used, thus largely avoiding extraneous light problems. The signal generated by the receiver is evaluated in such a way that changes in intensity of the transmitted light are established, whereby a threshold value for the change in intensity is set, from which a signal is generated which indicates the presence of an air or gas bubble or of a small solid foreign body in the liquid. Because it is not the absolute intensity but only changes in intensity which are measured, calibration of the bubble detector to a certain intensity is not necessary.

During the dispensing of very small quantities of liquid it may be necessary to take into account the evaporation of the liquid which takes place through the hose wall. If a certain quantity of liquid, e.g. liquid drops of the same size, is to be dispensed at different time intervals, the time elapsed since the last drop was dispensed is to be taken into account, by appropriate choice of the delivery volume, i.e. of the step angle, and the quantity of liquid evaporated within this time span to be made good. It is also to be taken into account here that a hose initially absorbs a certain amount of liquid when first used, with the result that evaporation is initially seemingly greater. In addition, the total length of the hose from the supply container to the dispensing device, the diameter of the hose, the wall thickness of the hose, the hose material and the liquid to be dispensed (adhesive) are to be taken into account.

An embodiment of the invention is described below with reference to the drawings.

Figure 1:
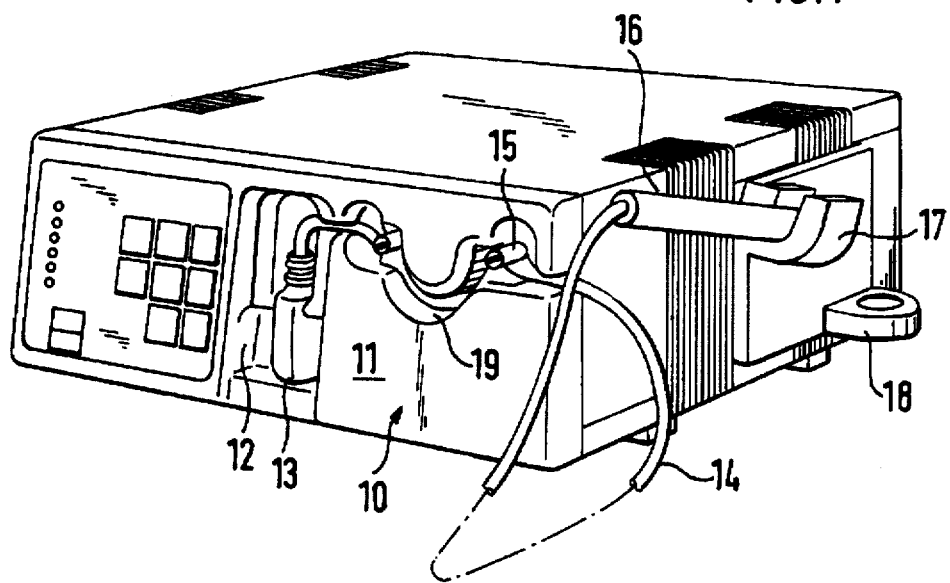
FIG. 1 depicts, an overall perspective view of a device for the dosing and application of a skin adhesive.

According to FIG. 1, the device for the dosing of a skin adhesive has a housing 10, in which the control system, which is not shown in detail, and the drive motor, which is likewise not shown, for the hose pump are contained. In the front 11 of the housing 10 there is a niche 12 for accommodating a bottle 13 which contains the skin adhesive to be dosed. A hose 14, which conveys the adhesive from the bottle 13 via a hose pump 15 to a dosing stylus 16 with which the adhesive is applied, is inserted into the bottle 13. A holster 17 is also provided on the same side of the housing 10 for the dosing stylus 16. Also situated on the same side of the housing 10 is a draining dish 18 into which the adhesive drips from the dosing stylus 16 when the dosing stylus 16 is in its holster 17. The hose pump 15 is located in the housing 10. In order to be able to insert the hose 14, which leads from the bottle 13 to the dosing stylus 16, into the hose pump 15, there is an incision 19 on the front 11 of the housing 10 which is shaped according to the course of the hose 14 through the hose pump 15, so that the hose 14 can be inserted through the incision 19 from outside into the hose pump 15. Easier insertability and replaceability of the hose 14 is especially important in the case of skin adhesive, since a new hose must frequently be used here.

Figure 2:
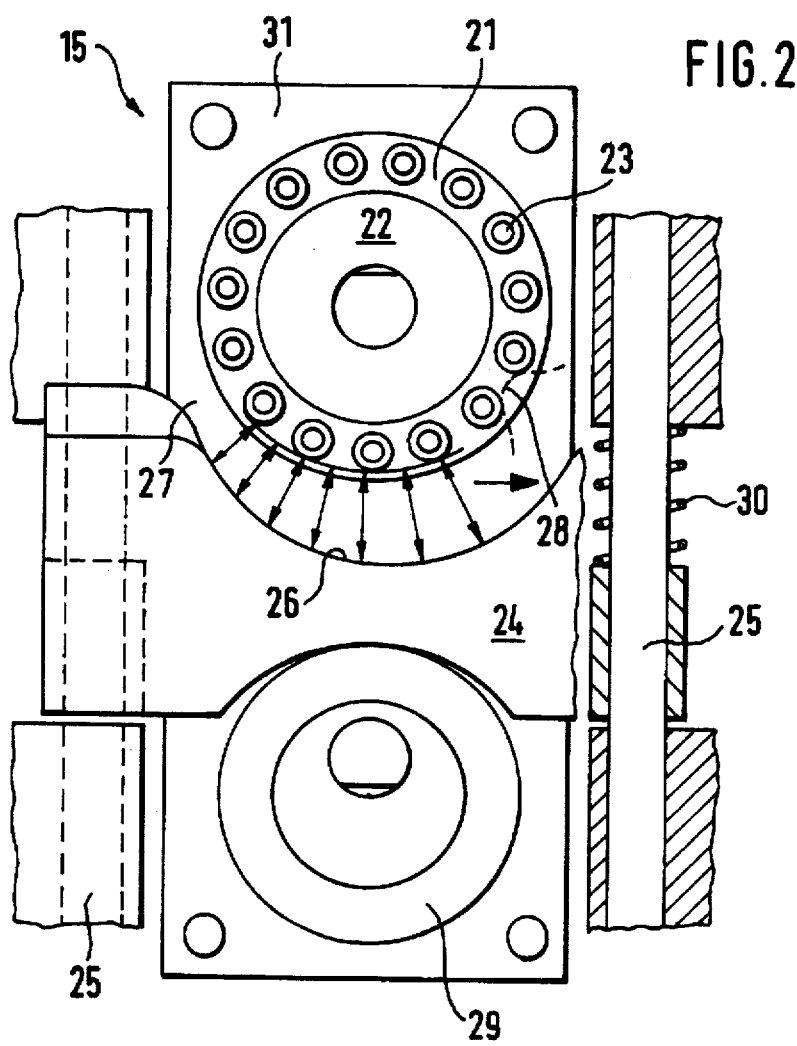
FIG. 2 depicts a front view in partial cross section of the hose pump according to the present invention contained in the device depicted in FIG. 1.

The details of the hose pump 15 are shown in FIG. 2. Rollers 23 are housed in freely rotatable manner with a certain division on a pitch circle 21 of a roller holder 22. The roller holder 22 is driven by a drive motor which is not shown. Positioned in height-adjustable manner at a distance below the roller holder is a hose bed 24. For this, the hose bed 24 is displaceably housed at both ends on guide rods 25. The surface of the hose bed 24 which is allocated to the rollers 23 is concave and thereby forms a trough 26 at a distance from the roller orbital path. The trough 26 is arranged eccentrically vis-à-vis the roller holder 22, and it is offset in approximately the direction of the delivery direction, marked by an arrow, which is preset by the rotational movement of the roller holder 22, so that the point of maximum contact pressure of the rollers 23 against the hose 14 lies at the entrance 27 of the trough 26. The distance between the rollers 23 and the trough 26 then always expands in the delivery direction, so that the space available for the hose 14 between the rollers 23 and the trough 26 opens in a conically curved manner. The sinusoidal periodic pump pulses are smoothed by the eccentric arrangement of the hose bed 24 and the curved conical aperture angle thereby achieved, with result of which is a seemingly continuous conveyance of the adhesive.

Matching the number and the diameter of the rollers 23 and the diameter of the pitch circle 21 on which the rollers 23 are arranged also contributes to achieving as continuous as possible a conveyance. So-called roller chambers form in the hose 14 between successive rollers 23. The roller chambers 28 must not be enlarged or reduced arbitrarily relative to the pitch circle diameter and the roller diameter since they are decisive for the conveyed quantity. An odd number of rollers 23 is especially advantageous for achieving a possibly continuous pump behaviour. This follows from the link between input size and output size in non-linear systems. The length of the trough 26 and the distance between the rollers 23 is also to be chosen such that there are always at least three rollers 23 in the trough 26.

Figure 4:
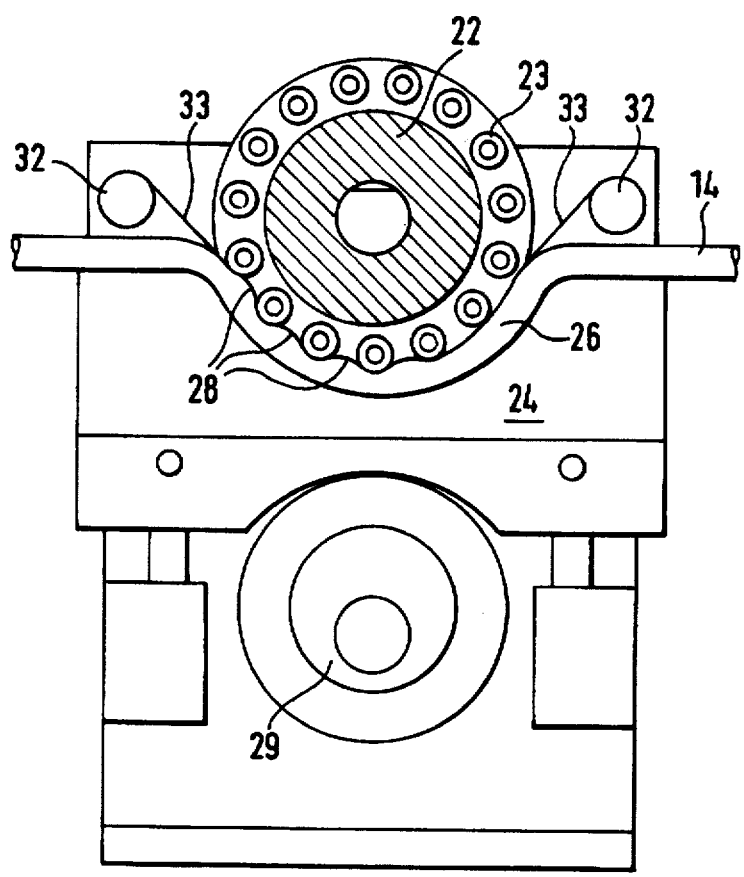

A protective film 33 is expediently placed between the rollers 23 and the hose 14 in order to absorb the tangential forces which are exerted by the rollers 23 onto the hose 14, and thereby to avoid displacement of the hose 14. In addition, by so doing the hose 14 does not adhere to the rollers 23. The protective film is shown, as is the hose 14, in FIG. 4. The protective film is a film strip, the width of which corresponds approximately with the length of the rollers 23. The protective film is held at its ends by means of the clamping bolts 32 recognizable in FIGS. 1 and 4.

To insert the hose 14 and optionally to replace the protective film 33, the hose pump 15 is opened by lifting the hose bed 24 some distance from the roller holder 22. For this, the hose bed 24 is displaceable on guide rods 25 by means of an eccentric roller 29 arranged beneath the hose bed 24. The hose pump 15 is shown in the opened state in FIG. 2 and in the closed state in FIG. 4. The hose bed 24 is pre-tensioned against the eccentric roller 29 by pressure springs 30. The roller holder 22 and the eccentric roller 29 are positioned in a motor bearer plate 31 and the hose bed 24 is located between them.

Figure 3:
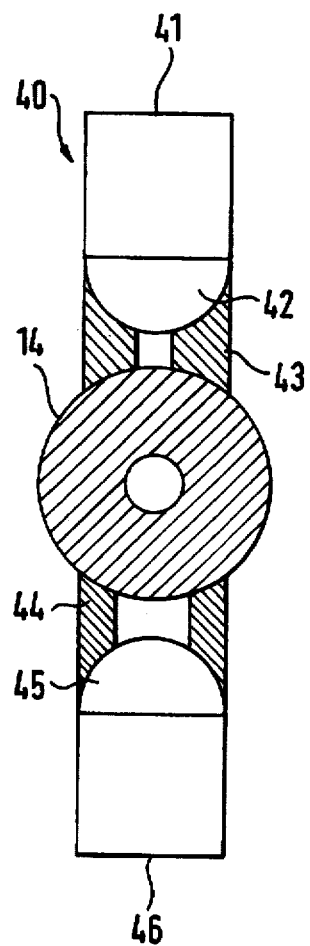
FIG. 3 depicts a top plan view in partial cross section of a bubble detector in partial cross sectional view as viewed along the hose axis and FIG. 4 depicts a front view in partial cross section of the hose pump according to the present invention with the laid hose passing therethrough and a protective film contacting the laid hose as it meets the rollers.

A bubble detector 40 is shown in FIG. 3 which is incorporated within the housing 10 shown in FIG. 1 between the niche 12 and the hose pump 15. The bubble detector 40 contains a transmitter 41 in the form of an infra-red diode, a first lens 42, which focuses the light from the transmitter 41, a first screen 43 which only allows through a light beam whose diameter is somewhat smaller than the internal diameter of the hose 14. A second screen 44 is arranged on the opposite side of the hose 14 which screens out external light shining in from the side. Arranged behind the screen is a second lens 45 which focuses the transmitted light on a receiver 46 in the form of a photo transistor. The wavelength of the light emitted by the transmitter 41 is based on the ratios in each case, in particular of the absorption of this wavelength by the material of the hose 14 and by the liquid flowing in the hose 14 and on the external light ratios. In the embodiment represented, infra-red light of a wavelength of 850–950 nm is used, to which end suitable interference filters are incorporated in the receiver 46. As mentioned, the diameter of the first screen 43 is somewhat smaller than the internal diameter of the hose 14. It is thereby ensured, even in the case of incomplete parallelism of the light beam, that no light passes by the liquid present in the hose 14 to the receiver 46. The diameter of the second screen 44 is expediently twice as large as the internal diameter of the hose 14.

The receiver 46 generates an electrical signal which is approximately proportional to the amount of light falling on it. If the hose 14 is filled with the liquid, part of the light is absorbed by the liquid and the receiver 46 generates an electrical signal. If air or gas bubbles or foreign bodies are in the liquid, the amount of light striking the receiver 46 momentarily changes while these air or gas bubbles or foreign bodies move through the bubble detector 40, with the result that the bubble detector generates a signal pulse. The signal from the receiver 46 is processed in an electronic network which is not shown, whereby the network generates an output signal with every change which is characteristic of the passage of a gas bubble or of a foreign body. Because the electronic network does not analyse the absolute value of the receiver signal, but only reacts to changes in the detector signal, calibration or setting of the bubble detector to a certain absolute signal value is not necessary.

The bubble detector is of course not only applicable in connection with the hose pump according to the invention, but can also be used in combination with other apparatuses or as an independent unit.

The device shown in FIG. 1 for the dosing and the application of a skin adhesive contains a control system which regulates the hose pump 15 in accordance with the control signals entered using a keyboard 50. The signals of the bubble detector 40 are also processed in the control system. Skin adhesive is generally applied dropwise by the surgeon. The control system chooses the step angle of the roller holder 20 according to the selected drop size. The control system for controlling the quantity of fluid dispensed does so by adjusting the angle defined by the roller holder, which has a central axis of rotation, with respect to the hose bed. The angle adjustments (or step angle) influence in part the quantity of fluid dispensed. A continuous operation of the hose pump 14 can moreover also be chosen for the first filling of the hose 14. Dispensing of each of the drops of the selected size is brought about by a foot switch (not shown).

The control system also takes into account the time span elapsed between two dispensing processes, which also influence in part the quantity of fluid dispensed. Most liquids, in particular adhesives, evaporate to a small extent through the wall of the hose 14, the material of the hose playing an essential role. When dosing particularly small quantities of liquids it is therefore important to compensate for the amount of liquid which has diffused through the hose 14, by making good this loss of liquid during the next dosing process. In addition, the control system also indicates by optical or acoustic signals when the processing time of the adhesive has expired.

This control system can be used generally and not only in conjunction with the hose pump according to the invention for the dispensing of liquids, in particular for the dispensing of small quantities of liquids at time intervals as desired. The control system regulates the dispensing device such that the time span which has elapsed between two dispensing processes is taken into consideration in order to compensate for liquid losses which have occurred in this time period by evaporation through the hose or absorption in the hose.

I claim:

1. An improved hose pump for dosing precise quantities of fluid comprising:
   a rotary-driven roller holder,
   a plurality of rotatable rollers housed on the roller holder in a pitched circle,
   a hose bed having a contoured surface facing the roller holder, each of said roller holder, rotatable rollers and hose bed being arranged such that the roller holder moves the rollers about an orbital path at a distance from the contoured face of the hose bed, said distance being such that the rollers can compress through a portion of the orbital path thereof a hose which, during operation of the pump, is placed between the hose bed and the orbital path of the rollers, through a portion of the orbital path thereof, and
   a control means for controlling the quantity of fluid dispensed, which is achieved through (a) adjusting an angle defined by the roller bed with respect to the hose bed, wherein angle adjustments influence the quantity of fluid dispensed and (b) the time elapsed since the previous dispensing of fluid so as to compensate for fluid losses which may have occurred,
   wherein the contour of the hose bed is offset from the orbital path of the rollers so that the distance between the hose bed and the orbital path of the rollers increases in the direction of movement of the rollers until the rollers reach a point where they are capable of exerting a minimum of compression on said hose.

2. A hose pump according to claim 1, wherein the contoured surface of the hose bed is in the configuration of a concave trough.

3. A hose pump according to claim 1, wherein the hose bed is pre-tensioned by spring tension against an eccentric roller which by rotating moves the hose bed between the first and second positions.

4. A hose pump according to claim 1, wherein an odd number of rollers is arranged on the roller holder.

5. A hose pump according to claim 1, wherein at least three rollers are positioned within the contoured surface of the hose bed.

6. A hose pump according to claim 1, further comprising a protective film between the rollers and the hose bed, said protective film being arranged between the rollers and the hose during operation of the pump.

7. A hose pump according to claim 1, further comprising a detector for detecting in a liquid conveyed through the hose, during operation of the pump, a member selected from the group consisting of gas bubbles and foreign bodies.

8. A hose pump according to claim 7, wherein the detector includes
   a transmitter,
   a receiver and
   a control means for processing the signal generated by the receiver so that a warning signal is generated when a change occurs in the quantity of light received by the receiver indicating the presence of a member selected from the group consisting of bubbles and foreign bodies.

9. A hose pump according to claim 8, wherein the detector further includes a screen which, in operation of the pump, resides between the transmitter and the hose, the aperture of said screen being smaller than the internal diameter of the hose but allowing the hose to fit therethrough and be retained thereby.

10. A hose pump according to claim 1 characterized in that the hose bed is moveable between a first and a second position relative to the roller holder.

11. A hose pump according to claim 10, wherein said rollers are capable of exerting a maximum compression on said hose at the start of the trough.

12. A hose pump according to claim 2, wherein said rollers are capable of exerting a maximum compression on said hose at a point which is displaced from the center of the trough opposite the direction of movement of the rollers.

13. A hose pump according to claim 2, further comprising a drive motor for rotating the roller holder.

14. A hose pump according to claim 13, wherein the control means controls the drive motor so as to control the rotation of the roller holder thereby adjusting the angle defined by the roller holder with respect to the hose bed.

15. A hose pump according to claim 1 wherein the contoured surface of the hose bed is eccentric to the orbital path of the rollers.

16. A hose pump according to claim 1, wherein the contoured surface of the hose bed is a circular arc whose axis is offset from the axis of the orbital path by approximately the internal diameter of the hose to be used in operation of the hose pump.

17. A hose pump according to claim 1 wherein the contoured surface of the hose bed is an eccentric arc.

* * * * *